United States Patent
Lawson et al.

(10) Patent No.: US 9,884,923 B2
(45) Date of Patent: *Feb. 6, 2018

(54) AMINOSILANE INITIATORS AND FUNCTIONALIZED POLYMERS PREPARED THEREFROM

(75) Inventors: David F. Lawson, Uniontown, OH (US); Terrence E. Hogan, Uniontown, OH (US); Christine Rademacher, Akron, OH (US); David M. Roggeman, North Royalton, OH (US); Fuminori Ota, Kodaira (JP)

(73) Assignee: Bridgestone Corporation, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,603

(22) PCT Filed: Dec. 30, 2010

(86) PCT No.: PCT/US2010/062455
§ 371 (c)(1),
(2), (4) Date: Nov. 16, 2012

(87) PCT Pub. No.: WO2011/082277
PCT Pub. Date: Jul. 7, 2011

(65) Prior Publication Data
US 2013/0066008 A1    Mar. 14, 2013

Related U.S. Application Data

(60) Provisional application No. 61/291,635, filed on Dec. 31, 2009.

(51) Int. Cl.
| | |
|---|---|
| C08F 4/48 | (2006.01) |
| C08F 4/58 | (2006.01) |
| C08F 4/618 | (2006.01) |
| C07F 7/10 | (2006.01) |
| C08F 236/10 | (2006.01) |
| C08F 136/06 | (2006.01) |
| C08L 9/06 | (2006.01) |
| B60C 1/00 | (2006.01) |
| C08F 297/02 | (2006.01) |
| C08F 297/04 | (2006.01) |
| C08F 290/04 | (2006.01) |
| C08F 212/08 | (2006.01) |

(52) U.S. Cl.
CPC .............. *C08F 4/486* (2013.01); *B60C 1/00* (2013.01); *C07F 7/10* (2013.01); *C08F 4/48* (2013.01); *C08F 4/58* (2013.01); *C08F 4/6185* (2013.01); *C08F 4/6186* (2013.01); *C08F 136/06* (2013.01); *C08F 236/10* (2013.01); *C08L 9/06* (2013.01); *B60C 1/0008* (2013.01); *B60C 1/0016* (2013.01); *B60C 1/0025* (2013.01); *B60C 2001/005* (2013.01); *B60C 2001/0033* (2013.01); *B60C 2001/0058* (2013.01); *B60C 2001/0066* (2013.01); *B60C 2001/0075* (2013.01); *B60C 2001/0083* (2013.01); *B60C 2001/0091* (2013.01); *C08F 212/08* (2013.01); *C08F 290/044* (2013.01); *C08F 290/048* (2013.01); *C08F 297/02* (2013.01); *C08F 297/04* (2013.01); *C08F 297/042* (2013.01); *C08F 297/044* (2013.01); *Y02T 10/862* (2013.01)

(58) Field of Classification Search
CPC .. C08F 297/02; C08F 297/04; C08F 297/048; C08F 297/042; C08F 297/044; C08F 290/044; C08F 290/048; C08F 4/48; C08F 4/58; C08F 4/6185; C08F 4/6186; B60C 1/00; B60C 1/0008; B60C 1/0016; B60C 1/0025; B60C 2001/0033; B60C 2001/005; B60C 2001/0058; B60C 2001/0066; B60C 2001/0075; B60C 2001/0083; B60C 2001/0091; Y02T 10/862
USPC .................. 526/194, 204, 217; 525/102
See application file for complete search history.

(56) References Cited

U.S. PATENT DOCUMENTS

| | | | |
|---|---|---|---|
| 3,445,425 A | 5/1969 | Speier | |
| 3,485,857 A * | 12/1969 | Speier | ........... C07F 7/10 556/12 |

(Continued)

FOREIGN PATENT DOCUMENTS

| | | |
|---|---|---|
| CN | 1961011 | 5/2007 |
| EP | 0225452 | 1/1990 |

(Continued)

OTHER PUBLICATIONS

Hirao, Akira et al., "Polymerization of Monomers Containing Functional Silyl Groups. 13. Anionic Polymerization of 2[(N,N-dialkylamino)dimethylsilyl]-1,3-butadiene Derivatives", 1998, Macromolecules, 31,281-287.*

(Continued)

*Primary Examiner* — Ling Choi
*Assistant Examiner* — David L Miller
(74) *Attorney, Agent, or Firm* — Meredith E. Hooker; Jenny L. Sheaffer

(57) ABSTRACT

Metallated aminosilane compounds for use as functional initiators in anionic polymerizations and processes for producing an aminosilane-functionalized polymer using the metallated aminosilane compounds to initiate anionic polymerization of at least one type of anionically polymerizable monomer. Preferred use of the metallated aminosilane compounds results in rubber compositions for use in tires comprising an aminosilane functionalized polymer.

21 Claims, No Drawings

(56) References Cited

U.S. PATENT DOCUMENTS

| | | | |
|---|---|---|---|
| 3,607,846 A | 9/1971 | Halasa et al. | |
| 4,616,069 A | 10/1986 | Watanabe et al. | |
| 4,771,116 A | 9/1988 | Citron et al. | |
| 4,771,117 A | 9/1988 | Citron et al. | |
| 5,128,416 A * | 7/1992 | Imai et al. | 525/254 |
| 5,189,109 A * | 2/1993 | Imai | C08C 19/42 |
| | | | 525/271 |
| 5,219,938 A | 6/1993 | Imai et al. | |
| 5,332,810 A | 7/1994 | Lawson et al. | |
| 5,362,699 A | 11/1994 | Shepherd et al. | |
| 5,496,940 A | 3/1996 | Lawson et al. | |
| 5,502,131 A | 3/1996 | Antkowiak et al. | |
| 5,527,753 A | 6/1996 | Engel et al. | |
| 5,565,526 A | 10/1996 | Schwindeman et al. | |
| 5,932,662 A | 8/1999 | Lawson et al. | |
| 6,349,753 B1 | 2/2002 | Lawson et al. | |
| 7,335,712 B2 | 2/2008 | Yan et al. | |
| 7,598,322 B1 | 10/2009 | Rademacher et al. | |
| 7,612,144 B2 | 11/2009 | Hogan et al. | |
| 8,415,435 B2 | 4/2013 | Oshima | |
| 2003/0088029 A1 | 5/2003 | Ozawa | |
| 2003/0135007 A1* | 7/2003 | Ewald et al. | 528/27 |
| 2006/0241241 A1 | 10/2006 | Yan et al. | |
| 2006/0264590 A1 | 11/2006 | Hogan et al. | |
| 2007/0161757 A1 | 7/2007 | Rademacher et al. | |
| 2008/0051552 A1 | 2/2008 | Luo et al. | |
| 2008/0103261 A1 | 5/2008 | Tanaka et al. | |
| 2009/0247692 A1* | 10/2009 | Oshima et al. | 524/547 |
| 2010/0056703 A1 | 3/2010 | Oshima | |
| 2010/0056712 A1 | 3/2010 | Oshima | |
| 2010/0317818 A1 | 12/2010 | Hogan et al. | |
| 2016/0152756 A1 | 6/2016 | Lawson et al. | |

FOREIGN PATENT DOCUMENTS

| | | | |
|---|---|---|---|
| EP | 0451603 | | 4/1990 |
| EP | 1734060 | | 12/2006 |
| EP | 1734060 | A1 | 12/2006 |
| EP | 2266819 | | 12/2010 |
| GB | 1217471 | | 12/1970 |
| JP | H01278529 | A | 11/1989 |
| JP | H02-240086 | | 4/1992 |
| JP | 2007-48930 | | 2/2007 |
| JP | 5551796 | B | 7/2014 |
| KR | 2009-0104727 | A | 10/2009 |
| WO | WO 0050478 | A1 * | 8/2000 |
| WO | 2008108377 | | 9/2008 |
| WO | 2009086490 | | 9/2009 |
| WO | WO2011082277 | A1 | 7/2011 |

OTHER PUBLICATIONS

Kitaura, Takehiro et al., "Anionic Polymerization of (Meth)acrylates with Trialkylsilyl-protected Lithium N-benzylamide," Polymer Journal, The Society of Polymer Science, Japan, vol. 40, No. 1, pp. 37-45 (Jan. 15, 2008).
Kitayama, Tatsuki et al., "Anionic Polymerization of Methyl Methacrylate with Lithium N-benzyitrimethylsilylamide," Polymer Journal, vol. 35, No. 6, pp. 539-543 (2003).
Stober, Marilyn R. et al., "The Polymerization of Vinylaminosilanes. The Unique Stability of Silicon-Nitrogen Bonds toward Alkyllithium Compounds," J. Org. Chem, vol. 32, Issue 9, pp. 2740-2744 (Sep. 1967).
Scheunemann, Sven, Apr. 1, 2011 International Search Report with Written Opinion from PCT/US2010/062455 (5 pp.).
Kitaura et al. "Anionic Polmerization of (Meth) Acrylates with Trialkylsilyl-Protected Lithium N-Benzylamide" Polymer Journal, Society of Polymer Science, Tokyo, JP, vol. 40, No. 1, Jan. 15, 2008.
Kitayama et al. "Anionic Polymerization of Methyl Methacrylate With Lithium N-Benzyltrimethylsilylamide" Polymer Journal 2003 Society of Polymer Science JP. vol. 35, No. 6, pp. 539-543, 2003.
International Search Report for PCT/US2011/041421 dated Oct. 19, 2011.
First Office Action from JP Application No. 2012-547287 dated Jan. 21, 2014.
Stober et al., J. Org Chem., 32, 2740 (1967).
First Office Action for U.S. Appl. No. 13/977,296 dated Apr. 8, 2014.
Styron et al., Journal of Organometallic Chemistry, 585, pp. 266-274 (1999).
First Office Action from CN Application No. 201080064998.1 dated Aug. 30, 2013.
Second Office Action from CN Application No. 201080064998.1 dated Feb. 20, 2014.
Rules 161 & 162 Commn Response dated Jan. 29, 2014.
Third Party Observations, dated Mar. 18, 2013.
First Office Action from EP Application No. 10 803 331.7-1301 dated Jul. 10, 2013.
Response to First Office Action from EP Application No. 10 803 331.7-1301 dated Nov. 12, 2013.
Written Opinion and International Preliminary Report on Patentability for PCT/US2010/062455 mailed Jul. 12, 2012.
Written Opinion and International Preliminary Report on Patentability for PCT/US2011/041421.
Non-Final Office Action for Japanese Application No. 2013-547453 dated Nov. 11, 2014.
Nutt et al., Inorg. Chem., vol. 30 No. 22, pp. 4136-4140, (1991).
Tamao et al., Tetrahedron Letters, vol. 25, No. 18, pp. 1909-1912 (1984).
Notification of Reasons for Refusal, issued in application JP 2014-106430 (dated Apr. 28, 2015).
First Office Action, issued in CN 201180062089.9 (dated Apr. 3, 2015).
Non-final rejection in U.S. Appl. No. 14/570,078 (issued Jun. 5, 2015).
Communication pursuant to Article 94(3) EPC, issued in EP Application No. 10 803 331 (dated Apr. 30, 2015).
Mulvey, Robert E., "An alternative picture of alkali-metal-mediated metallation: cleave and capture chemistry," Dalton Transactions, vol. 42 No. 19, May 21, 2013, pp. 6676-6693.
Mulvey, Robert E., "Avante-Garde Metalating Agents: Structural Basis of Alkali-Metal-Mediated Metalation," Accounts of Chemical Research, vol. 42 No. 6, Jun. 2009, pp. 743-755.
Response filed on Jul. 30, 2015 in U.S. Appl. No. 14/570,078.
Office Action issued in application JP 2014-106430 (issued Jul. 21, 2015).
Opposition notice from EP 2658727B1 with letter dated Sep. 3, 2015.
Third Office Action from application No. CN201180062089.9 (issued Apr. 25, 2016).
Statement of Response of Patent Proprietor filed in opposition proceedings for EP2658727B1 (filed Feb. 29, 2016), with auxiliary claims attached.
Second Office Action from application No. CN201180062089.9 (issued Nov. 18, 2015).
Letter of Patentee in Opposition of Patent EP2658727B1/application No. EP11729524.6 (dated May 18, 2017), 110 pages.
Fourth Office Action from application No. CN201180062089.9 (issued Jul. 2016).
Office Action from application No. JP2015-221518 (issued Jul. 2016).
Preliminary Amendment from U.S. Appl. No. 15/014,620, filed Feb. 8, 2016.
Office Action from U.S. Appl. No. 15/014,620 (issued Oct. 3, 2016).
Response from U.S. Appl. No. 15/014,620, filed Dec. 15, 2016.
Summons to Oral Hearing in Opposition of Patent EP2658727B1/application No. EP11729524.6 (issued Nov. 18, 2016).
Letter of Opponent in Opposition of Patent EP2658727B1/application No. EP11729524.6 (dated May 19, 2016).
Letter of Patentee in Opposition of Patent EP2658727B1/application No. EP11729524.6 (dated Jul. 17, 2017) with auxiliary claim sets, 41 pages.
Letter of Opponent in Opposition of Patent EP2658727B1/application No. EP11729524.6 (dated Jul. 11, 2017), 7 pages.

(56) References Cited

OTHER PUBLICATIONS

Decision revoking patent in Opposition of Patent EP2658727B1/ application No. EP11729524.6 (dated Aug. 7, 2017), 33 pages.
Minutes from hearing in Opposition of Patent EP2658727B1/ application No. EP11729524.6 (dated Aug. 7, 2017) with claims annex, 14 pages.
Mark, James E., et al. editor, The Science and Technology of Rubber, Third Edition, copyright 2005, p. 513.
Iupac, Copendium of Chemical Terminology, 2nd Ed. (the "Gold Book"), definition of telechelic polymer, last updated Feb. 24, 2014, printed Jul. 11, 2017.
Office action rejection from Korean patent application 10-2012-7020090 (dated Jun. 21, 2017), 11 pages.

\* cited by examiner

AMINOSILANE INITIATORS AND FUNCTIONALIZED POLYMERS PREPARED THEREFROM

CROSS-REFERENCE TO RELATED APPLICATIONS

This application is a U.S. national stage application of International Application Number PCT/US2010/062455, filed Dec. 30, 2010, which claims priority to and the benefit of the U.S. Provisional Patent Application Ser. No. 61/291,635, filed Dec. 31, 2009, both of which are hereby incorporated by reference in their entirety.

FIELD OF INVENTION

The present application relates to silane-functionalized polymers and rubber vulcanizates prepared therefrom.

BACKGROUND

In the art of making tires, it can be desirable to employ rubber vulcanizates that demonstrate reduced hysteresis loss, i.e., less loss of mechanical energy to heat. Hysteresis loss is often attributed to polymer free ends within the cross-linked rubber network, as well as the disassociation of filler agglomerates.

Functionalized polymers have been employed to reduce hysteresis loss and increase bound rubber. The functional group of the functionalized polymer is believed to reduce the number of polymer free ends. Also, the interaction between the functional group and the filler particles reduces filler agglomeration, which thereby reduces hysteretic losses attributable to the disassociation of filler agglomerates. The present application stems from a recognition that an aminosilane ("silazane") functional group within the polymer portion of a rubber vulcanizate has been found to improve the physical properties of the rubber vulcanizate. The aminosilane functionality in the polymer presumably improves the interaction of the polymer with additional components, such as silica fillers. This improved interaction often translates into improved mixing and better dispersion of ingredients.

SUMMARY

The present application provides metallated aminosilane compounds for initiating anionic polymerizations.

The present application also provides processes for producing an aminosilane-functionalized polymer comprising the steps of providing an initiator by preparing a metallated aminosilane compound, either pre-formed or in situ, and polymerizing at least one type of anionically polymerizable monomer using the metallated aminosilane compound to initiate the polymerization.

The present application also provides a rubber composition for use in tires comprising an aminosilane functionalized polymer that has been made according to the processes disclosed herein.

DETAILED DESCRIPTION

This application provides functionalized initiators in the form of particular metallated aminosilane compounds useful for anionic polymerization. Polymers prepared using these initiators contain a functional group at the head of the polymer chain, and it has been discovered that vulcanizable elastomeric compounds and articles thereof based upon such functional polymers exhibit useful properties. In general, the "head" of a polymer is the chain end where initiator residue resides, whereas the "tail" is the chain end nearest the location where the final monomer unit has been added to the polymer. As used herein, the term "at the head" and "at the tail" mean locations at or near the head and tail, respectively.

Use of the metallated aminosilane compounds disclosed herein to initiate anionic addition polymerization (or copolymerization) allows for the production of aminosilane-functionalized polymers having the silicon of the aminosilane group directly bonded to the end of a polymer chain through one or more carbon atoms. Directly bonding the silicon of the aminosilane to the head of the polymer chain through one or more carbon bonds allows for an increased likelihood that silicon will remain bound to the polymer chain throughout the polymerization reaction and any subsequent processing of the polymer with rubber vulcanizate materials. Without wishing to be bound by theory, it is believed that the aminosilane-functional polymer may react by hydrolysis and condense with fillers in rubber vulcanizate compounds to give improved filler microdispersion, resulting in reduced hysteresis rubber vulcanizate compounds that are useful in improving fuel economy of tires made therefrom.

In one embodiment, the present application discloses a metallated aminosilane compound for initiating an anionic polymerization comprising the reaction product of at least one metallating agent and at least one alkylaminosilane compound having the formula

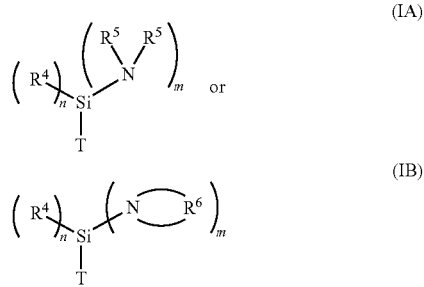

where n is a whole number selected from the group consisting of 0-2, and m is a whole number selected from the group consisting of 1-3, with the proviso that the sum of m and n equals 3; where T is a methyl, ethyl, propyl, or allylic group; where each $R^4$ and $R^5$ is independently a hydrocarbyl group; where each $R^6$ is independently a hydrocarbylene; and where one or more $R^5$ may form a bridge between two nitrogen atoms when m is greater than 1.

In general, the aminosilane compounds of the present application may be any compound that contains between one and three dihydrocarbylamino groups bonded directly to a silicon atom. The aminosilane compounds may contain various other hydrocarbyl or phenyl groups in addition to dihydrocarbylamino groups.

Alkylaminosilane compounds described in the present application are aminosilane compounds that have at least one alkyl or allylic group ("T" or "tether" group) directly bonded to the silicon atom. As used herein, the term "allylic group" refers to any substituted or unsubstituted allylic group

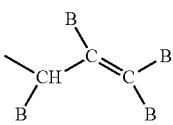

bonded to the silicon atom. The allylic group may contain one or more hydrogen, alkyl or aryl substituents (B). In general, T is selected in a manner such that the metallating reagent may abstract a proton and the metal-alkyl bond generated initiates polymerization. Non-limiting examples of T are methyl, ethyl, propyl and allyl groups.

In one embodiment, the alkylaminosilane compound is selected from the group consisting of alkyleneiminodihydrocarbylalkylsilane, bis-(alkyleneimino)hydrocarbylalkylsilane, tris-(alkyleneimino)alkylsilane, aryleneiminodihydrocarbylalkylsilane, bis-(aryleneimino)hydrocarbylalkylsilane, tris-(aryleneimino)alkylsilane, dialkylaminodihydrocarbylalkylsilane, bis-(dialkylamino)hydrocarbylalkylsilane, tris-(dialkylamino)alkylsilane, diarylaminodihydrocarbylalkylsilane, bis-(diarylamino)hydrocarbylalkylsilane, tris-(diarylamino)alkylsilane, and combinations thereof. In another embodiment, the alkylaminosilane compound is selected from the group consisting of alkyleneiminodihydrocarbylallylsilane, bis-(alkyleneimino)hydrocarbylallylsilane, tris-(alkyleneimino)allylsilane, aryleneiminodihydrocarbylallylsilane, bis-(aryleneimino)hydrocarbylallylsilane, tris-(aryleneimino)allylsilane, dialkylaminodihydrocarbylallylsilane, bis-(dialkylamino)hydrocarbylallylsilane, tris-(dialkylamino)allylsilane, diarylaminodihydrocarbylallylsilane, bis-(diarylamino)hydrocarbylallylsilane, tris-(diarylamino)allylsilane, and combinations thereof. Preferably, the alkylaminosilane compound is selected from the group consisting of bis-(dialkylamino)phenylmethylsilane, bis-(hexamethyleneimino)phenylmethylsilane, tris-(dialkylamino)allylsilane, and combinations thereof. It is specifically contemplated that other alkylaminosilane compounds can be utilized.

Metallation, as is well-known in the art, typically involves a process where a proton of an organic compound is replaced with a metal. The metal is usually derived from an organometallic compound. Metallating an aminosilane compound to form an initiator, as described herein, may be accomplished in various ways.

Generally, the metallating agent is any compound capable of metallating an alkylaminosilane. The metallating agent operates by deprotonating an organic substituent of the aminosilane—typically the alkyl or allylic tether group T. Metallation via deprotonation may require a more highly basic solution than that required by a metallation via addition. In this regard, deprotonation may be encouraged by appropriate selection of metallating agent. For example, the use of sec- or tert-butyl lithium typically encourages metallation of an alkylaminosilane compound. In addition, deprotonation may be encouraged through the use of a metallating agent in conjunction with a Lewis base. Non-limiting examples of organic Lewis bases include ethers, amines, phosphines, sulfoxides, phosphoramides, and Grignard reagents. A mixture of any of these (or others) may be used.

In another embodiment, deprotonation may be encouraged through the use of a metallating agent in conjunction with a reagent selected from the group consisting of alkali metal alkoxide (e.g., Lochmann's base), alkali metal arylsulfonate, and combinations thereof.

Non-limiting examples of metallating agents include organometallic compounds such as hydrocarbyl lithium compounds, hydrocarbyl sodium compounds, hydrocarbyl potassium compounds, hydrocarbyl magnesium compounds, and combinations thereof. Preferably, the metallating agent is a hydrocarbyl lithium or hydrocarbyl sodium compound, or combinations thereof. Typically, the metallating agent is a hydrocarbyl lithium compound having the general formula C—Li, where C is selected from the group consisting of alkyls, cycloalkyls, alkenyls, aryls, and aralkyls having from 1 to 20 carbon atoms. Typical alkyls include but are not limited to isopropyl, butyl isomers, and pentyl isomers.

The metallated aminosilane initiator may optionally be pre-formed by pre-mixing the metallating agent and the alkylaminosilane compound (collectively, "ingredients") in the absence of the monomer to be polymerized, at an appropriate temperature (generally between −20° C. to 80° C.), and the resulting reaction product may be aged for a period of time ranging from a few seconds to a few days and then mixed with the monomer solution. If a Lewis base or other basic reagent is utilized, it may also be added to the mixture at this point. In pre-forming the initiator, an organic solvent or carrier may be employed, where it may serve to dissolve the ingredients. Alternatively, the solvent may simply serve as a carrier. Any organic solvent utilized is preferably inert to the metallated aminosilane compound and other ingredients. Useful solvents include polar and nonpolar hydrocarbon solvents such as aromatic hydrocarbons, aliphatic hydrocarbons, and cycloaliphatic hydrocarbons. Mixtures of such hydrocarbons may also be used.

In another embodiment, the metallated aminosilane initiator may optionally be formed in situ. Generally, the in situ preparation of anionic initiator is practiced by creating a solution comprising a polymerization solvent, if any, and one or more of the monomer(s) to be polymerized, and by mixing the aminosilane compound and metallating agent with the solution. Process conditions are adjusted so as to allow for the formation of a solution (cement) containing the desired functional polymer. Process conditions, such as reaction time and temperature may vary as necessary to allow the aminosilane compound and metallating agent to react, and subsequently polymerize the monomer solution.

In one embodiment of the present application, a process for producing an aminosilane-functionalized polymer comprises the steps of: (a) providing a pre-formed anionic initiator by preparing a metallated aminosilane compound comprising the reaction product of at least one metallating agent and at least one compound having formula (IA) or (IB), and (b) polymerizing at least one type of anionically polymerizable monomer by using the metallated aminosilane compound to initiate the polymerization.

A pre-formed metallated aminosilane initiator may be prepared by reacting a metallating agent and at least one compound having formula (IA) or (IB) in the manner discussed above. At least one type of anionically polymerizable monomer is then polymerized in the presence of the metallated aminosilane compound under typical polymerization conditions, as discussed below.

The principles of anionic addition polymerization and living polymerization are known to those of skill in the art. Anionically polymerized polymers may be prepared by either batch, semi-batch or continuous methods. In general, a batch polymerization is started by charging a blend of monomer(s) and solvent to a suitable reaction vessel, followed by the addition of a polar coordinator (if employed) and an initiator compound. The reactants are heated to a suitable temperature (generally from about 20° C. to about 130° C.) and the polymerization is allowed to proceed for a sufficient time (generally from about 0.1 to about 24 hours). The reaction produces a polymer having a reactive or living end. Unlike a continuous polymerization, initiator is not continuously added to reactor, and reaction product is not continuously removed.

In a semi-batch polymerization the reaction medium and initiator are added to a reaction vessel, and the monomer(s) is continuously added over time at a rate dependent on temperature, monomer/initiator/modifier concentrations, etc. Unlike a continuous polymerization, the product is not continuously removed from the reactor.

Generally, in a continuous polymerization reaction, the monomer(s), initiator and solvent are charged as feed streams to a suitable reaction vessel at the same time. Thereafter, a continuous procedure is followed that removes the product after a suitable residence time. In certain embodiments, additional feed streams may be present to charge additional components to the reaction vessel, including but not limited to reaction modifiers, functionalizing agents, terminating agents, and the like. In certain embodiments, one or more of the feed streams may be combined prior to charging the reaction vessel, in order to pre-form a component, including but not limited to initiators. In other embodiments, one or more reactions may be accomplished after the living polymer has been removed from the continuous polymerization reactor, including but not limited to functional termination of the polymer. Additional information relating to the principles of continuous polymerization and continuous polymerization reactors is disclosed in U.S. Pat. Nos. 5,231,152; 5,610,227; 6,362,282; 6,451,935; 6,881,795; 6,897,270; and 7,442,748, the disclosures of which are incorporated by reference herein.

The polymerization processes described herein involve at least one anionically polymerizable monomer and optionally additional comonomers. In general, all known anionically polymerizable monomers may be used. Non-limiting examples of anionically polymerizable monomers include conjugated dienes and vinyl aromatics, preferably conjugated dienes having from 4 to 12 carbon atoms and monovinyl aromatics having from 8 to 18 carbon atoms, and more preferably conjugated butadienes and pentadienes, isoprene, myrcene, and styrene.

Anionic polymerizations are typically conducted in a polar solvent, such as tetrahydrofuran (THF), or a non-polar hydrocarbon, such as the various cyclic and acyclic hexanes, heptanes, octanes, pentanes, their alkylated derivatives, and mixtures thereof, as well as benzene.

In order to promote randomization in copolymerization and to control vinyl content, a polar coordinator (modifier) may be added to the polymerization ingredients. The use of polar coordinators is known to those of skill in the art, and the use of suitable polar coordinators is within the scope of this application. Whether to use a polar coordinator and the amount of modifier to use depends on a number of factors, including but not limited to the amount of vinyl content desired and the temperature of the polymerization, as well as the nature of the specific polar coordinator employed. Typically, useful polar coordinators include compounds having an oxygen or nitrogen heteroatom and a non-bonded pair of electrons. Non-limiting examples include dialkyl ethers of mono and oligo alkylene glycols; "crown" ethers; tertiary amines such as tetramethylethylene diamine (TMEDA); and linear THF oligomers. Preferable polar coordinators include but are not limited to tetrahydrofuran (THF), linear and cyclic oligomeric oxolanyl alkanes such as 2,2-bis(2'-tetrahydrofuryl) propane, dipiperidyl ethane, dipiperidyl methane, hexamethylphosphoramide, N,N'-dimethylpiperazine, diazabicyclooctane, dimethyl ether, diethyl ether, tributylamine and the like. Linear and cyclic oligomeric oxolanyl alkane modifiers are described in U.S. Pat. No. 4,429,091, incorporated herein by reference.

The amount of metallated aminosilane initiator employed in conducting the anionic polymerizations described herein can vary widely based upon the desired polymer characteristics. In one embodiment, the metal to monomer molar ratio may be from 1:10 to 1:20,000. By metal is meant the metal in the metallated aminosilane compound or in the metallating agent. Likewise, in one embodiment, the metal to alkylaminosilane compound molar ratio may be from 0.8 to 1.2.

Initiating polymerization of at least one type of anionically polymerizable monomer by using the metallated aminosilane initiator described herein and propagating the polymerization are described above. In general, once a desired conversion is achieved, the polymerization can be stopped by terminating or coupling. One manner of terminating a polymerization is by protonating the living polymer by adding a compound that can donate a proton to the living end. Non-limiting examples include water, and isopropyl and methyl alcohol, and any mixtures thereof.

In one or more embodiments, the living polymer can be coupled to link two or more living polymer chains together. Those skilled in the art appreciate that the ability to couple polymer chains may depend upon the amount of coupling agent reacted with the polymer chains. For example, advantageous coupling may be achieved where the coupling agent is added in a one to one ratio between the equivalents of lithium on the initiator and equivalents of leaving groups (e.g., halogen atoms) on the coupling agent. Non-limiting examples of coupling agents include metal halides, metalloid halides, alkoxysilanes, and alkoxystannanes.

In one or more embodiments, metal halides or metalloid halides may be selected from the group comprising compounds expressed by the formula (1) $R^*_n M^1 Y_{(4-n)}$, the formula (2) $M^1 Y_4$, and the formula (3) $M^2 Y_3$, where each R* is independently a monovalent organic group having 1 to 20 carbon atoms, $M^1$ is a tin atom, silicon atom, or germanium atom, $M^2$ is a phosphorous atom, Y is a halogen atom, and n is an integer of 0-3.

Exemplary compounds expressed by the formula (1) include halogenated organic metal compounds, and the compounds expressed by the formulas (2) and (3) include halogenated metal compounds.

In the case where $M^1$ represents a tin atom, the compounds expressed by the formula (1) can be, for example, triphenyltin chloride, tributyltin chloride, triisopropyltin chloride, trihexyltin chloride, trioctyltin chloride, diphenyltin dichloride, dibutyltin dichloride, dihexyltin dichloride, dioctyltin dichloride, phenyltin trichloride, butyltin trichloride, octyltin trichloride and the like. Furthermore, tin tetrachloride, tin tetrabromide and the like can be exemplified as the compounds expressed by formula (2).

In the case where $M^1$ represents a silicon atom, the compounds expressed by the formula (1) can be, for example, triphenylchlorosilane, trihexylchlorosilane, trioctylchlorosilane, tributylchlorosilane, trimethylchlorosilane, diphenyldichlorosilane, dihexyldichlorosilane, dioctyldichlorosilane, dibutyldichlorosilane, dimethyldichlorosilane, methyltrichlorosilane, phenyltrichlorosilane, hexyltrichlorosilane, octyltrichlorosilane, butyltrichlorosilane, methyltrichlorosilane and the like. Furthermore, silicon tetrachloride, silicon tetrabromide and the like can be exemplified as the compounds expressed by the formula (2). In the case where $M^1$ represents a germanium atom, the compounds expressed by the formula (1) can be, for example, triphenylgermanium chloride, dibutylgermanium dichloride, diphenylgermanium dichloride, butylgermanium trichloride and the like. Furthermore, germanium tetrachloride, germanium tetrabromide and the like can be exemplified as the compounds expressed by the formula (2). Phosphorous trichloride, phosphorous tribromide and the like can be exemplified as the compounds expressed by the formula (3). In one or more embodiments, mixtures of metal halides and/or metalloid halides can be used.

In one or more embodiments, alkoxysilanes or alkoxystannanes may be selected from the group comprising compounds expressed by the formula (4) $R^*_n M^1(OR^{\wedge})_{4-n}$, where each $R^*$ is independently a monovalent organic group having 1 to 20 carbon atoms, $M^1$ is a tin atom, silicon atom, or germanium atom, $OR^{\wedge}$ is an alkoxy group where $R^{\wedge}$ is a monovalent organic group, and n is an integer of 0-3.

Exemplary compounds expressed by the formula (4) include tetraethyl orthosilicate, tetramethyl orthosilicate, tetrapropyl orthosilicate, tetraethoxy tin, tetramethoxy tin, and tetrapropoxy tin.

An antioxidant may be added along with, before, or after the addition of the terminating agent. When the polymerization has been stopped, the polymer can be recovered from the polymerization mixture by utilizing conventional procedures of desolventization and drying. For instance, the polymer may be isolated from the solution by coagulation of the polymerization mixture with an alcohol such as methanol, ethanol, or isopropanol, followed by isolation, or by steam distillation of the solvent and the unreacted monomer, followed by isolation. The isolated polymer is then dried to remove residual amounts of solvent and water. Alternatively, the polymer may be isolated from the polymerization mixture by evaporating the solvent, such as by directly drum drying the polymerization cement.

In another embodiment of the present application, a rubber composition for use in tires is provided comprising an aminosilane-functionalized polymer made by the processes described previously, at least one rubbery polymer, and at least one filler.

The aminosilane-functionalized polymers, and rubber compositions containing such functionalized polymers, as described in this application are particularly useful in preparing tire components. These tire components may be prepared by using the aminosilane-functionalized polymers described in this application alone or together with other rubbery polymers. The aminosilane-functionalized polymers are formed by initiating at least one type of anionically polymerizable monomer using a pre-formed anionic initiator comprising the reaction product of at least one metallating agent and at least one compound having formula (IA) or (IB), as described above. In another embodiment, the aminosilane-functionalized polymers are formed by initiating at least one type of anionically polymerizable monomer using a metallated aminosilane compound formed in situ, as described above.

Other rubbery polymers that may be used include natural and synthetic elastomers. Non-limiting examples of useful rubbery elastomers include natural rubber, synthetic polyisoprene, polybutadiene, poly(isobutylene-co-isoprene), neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Preferred elastomers include natural rubber, polybutadiene, polyisoprene, and the various copolymers of styrene, butadiene, and isoprene, because of their common usage in the tire industry.

Typically, in the rubber compositions disclosed herein, the aminosilane-functionalized polymer(s) is present in an amount ranging from 10 to 100 phr, whereas the other rubbery polymer(s) is present in an amount ranging from 0 to 90 phr.

The rubber compositions may include fillers such as inorganic and organic fillers, and mixtures thereof. Non-limiting examples of organic fillers include carbon black and starch, and mixtures thereof. Non-limiting examples of inorganic fillers include silica, aluminum hydroxide, magnesium hydroxide, clays (hydrated aluminum silicates), and mixtures thereof.

In one or more embodiments, silica (silicon dioxide) includes wet-process, hydrated silica produced by a chemical reaction in water, and precipitated as ultra-fine spherical particles. In one embodiment, the silica has a surface area of about 32 to about 400 $m^2/g$, in another embodiment about 100 to about 250 $m^2/g$, and in yet another embodiment, about 150 to about 220 $m^2/g$. The pH of the silica filler in one embodiment is about 5.5 to about 7 and in another embodiment about 5.5 to about 6.8. Commercially available silicas include Hi-Sil™ 215, Hi-Sil™ 233, Hi-Sil™ 255LD, and Hi-Sil™ 190 (PPG Industries; Pittsburgh, Pa.), Zeosil™ 1165MP and 175GRPlus (Rhodia), Vulkasil™ (Bary AG), Ultrasil™ VN2, VN3 (Degussa), and HuberSil™ 8745 (Huber).

In one or more embodiments, the carbon black(s) may include any of the commonly available, commercially-produced carbon blacks. These include those having a surface area (EMSA) of at least 20 $m^2$/gram and in other embodiments at least 35 $m^2$/gram up to 200 $m^2$/gram or higher. Surface area values include those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks that may be utilized include acetylene blacks. Mixtures of two or more of the above blacks can be used in preparing the carbon black products of the invention. Exemplary carbon blacks include those bearing ASTM designation (D-1765-82a) N-110, N-220, N-339, N-330, N-351, N-550, and N-660. In one or more embodiments, the carbon black may include oxidized carbon black.

In one embodiment, silica may be used in an amount of from about 5 to about 200 parts by weight parts per hundred rubber (phr), in another embodiment from about 10 to about 150 phr, in yet another embodiment from about 15 to about 80 phr, and in still another embodiment from about 25 to about 75 phr.

In one embodiment, carbon black may be used in an amount of from about 1 to about 200 phr, in an amount of about 5 to about 100 phr, or alternatively in an amount of about 30 to about 80 phr.

A multitude of rubber curing agents may be employed, including sulfur or peroxide-based curing systems. Curing agents are described in Kirk-Othmer, ENCYCLOPEDIA OF CHEMICAL TECHNOLOGY, Vol. 20, pgs. 365-468, ($3^{rd}$ Ed. 1982), particularly *Vulcanization Agents and Auxiliary Materials*, pgs. 390-402, and A. Y. Coran, *Vulcanization*, ENCYCLOPEDIA OF POLYMER SCIENCE AND ENGINEERING, ($2^{nd}$ Ed. 1989), which are incorporated herein by reference. Vulcanizing agents may be used alone or in combination. In one or more embodiments, the preparation of vulcanizable compositions and the construction and curing of the tire is not affected by the practice of this invention.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers. Examples of oils include paraffinic oils, aromatic oils, naphthenic oils, vegetable oils other than castor oils, and low PCA oils including MES, TDAE, SRAE, and heavy naphthenic oils.

These stocks are useful for forming tire components such as treads, subtreads, black sidewalls, body ply skims, bead filler, and the like. Preferably, the functional polymers are employed in tread formulations. In one or more embodiments, these tread formulations may include from about 10 to about 100% by weight, in other embodiments from about 35 to about 90% by weight, and in other embodiments from about 50 to 80% by weight of the functional polymer based on the total weight of the rubber within the formulation.

In one or more embodiments, the vulcanizable rubber composition may be prepared by forming an initial masterbatch that includes the rubber component and filler (the rubber component optionally including the functional polymer of this invention). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mix stage, which preferably does not initiate the vulcanization process. Optionally, additional mixing stages, sometimes called remills, can be employed between the masterbatch mix stage and the final mix stage. Various ingredients including the functional polymer of this invention can be added during these remills. Rubber compounding techniques and the additives employed therein are generally known as disclosed in *The Compounding and Vulcanization of Rubber*, in *Rubber Technology* ($2^{nd}$ Ed. 1973).

The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference. In one or more embodiments, where silica is employed as a filler (alone or in combination with other fillers), a coupling and/or shielding agent may be added to the rubber formulation during mixing. Useful coupling and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference. In one embodiment, the initial masterbatch is prepared by including the functional polymer of this invention and silica in the substantial absence of coupling and shielding agents. It is believed that this procedure will enhance the opportunity that the functional polymer will react or interact with silica before competing with coupling or shielding agents, which can be added later curing remills.

Where the vulcanizable rubber compositions are employed in the manufacture of tires, these compositions can be processed into tire components according to ordinary tire manufacturing techniques including standard rubber shaping, molding and curing techniques. Any of the various rubber tire components can be fabricated including, but not limited to, treads, sidewalls, belt skims, and carcass. Typically, vulcanization is effected by heating the vulcanizable composition in a mold; e.g., it may be heated to about 140 to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. Pneumatic tires can be made as discussed in U.S. Pat. Nos. 5,866,171, 5,876,527, 5,931,211, and 5,971,046, which are incorporated herein by reference.

Additional information relating to the use of fillers, including carbon black and silica fillers, and additional ingredients in rubber compositions for use in tire components, and information relating to compounding such formulations, is disclosed in U.S. Pat. Nos. 7,612,144, 6,221,943, 6,342,552, 6,348,531, 5,916,961, 6,252,007, 6,369,138, 5,872,176, 6,180,710, 5,866,650, 6,228,908 and 6,313,210, the disclosures of which are incorporated by reference herein.

The practice of the invention is further illustrated by the following examples, which should not be construed as limiting the scope of the invention as recited in the claims.

General Experimental Testing Procedures

Molecular Weight Determination: Molecular weights were measured by gel permeation/size exclusion chromatography (SEC) using a Waters Model 150-C instrument equipped with a Model 2414 Refractometer and a Model 996 Photodiode Array Detector (UV). Molecular weights were calculated from a universal calibration curve based on polystyrene standards and corrected using the following Mark-Houwink constants for SBR: k=0.000269, $\alpha$=0.73.

NMR: Styrene and vinyl content, and small molecule structure confirmation were determined using $^1$H-NMR (CDCl$_3$) and $^{13}$C NMR measurements on a 300 MHz Gemini 300 NMR Spectrometer System (Varian).

Glass Transition Temperature (Tg): The glass transition temperature was determined using a DSC 2910 Differential Scanning calorimeter (TA Instruments). The Tg was determined as the temperature where an inflection point occurred in the heat capacity (Cp) change.

Dynamic Mechanical Properties: The dynamic mechanical properties were measured using two techniques. A Rheometrics Dynamic Analyzer RDAII (Rheometric Scientific) in the parallel plate mode was used with 15 mm thick, 9.27 mm diameter buttons. The loss modulus, G", storage modulus, G', and tan $\delta$ were measured over deformation of 0.25-14.5% $\gamma$ at 1 Hz and 50° C. The Payne Effect was estimated by calculating the difference of G' (0.25% $\gamma$)–G' (14.0% $\gamma$). A RDA700 (Rheometric Scientific) in the torsion rectangular mode was also used with samples having the dimensions 31.7 mm×12.7 mm×2.0 mm. The temperature was increased at a rate of 5° C. min$^{-1}$ from –80° C. to 100° C. The moduli (G' and G") were obtained using a frequency of 5 Hz and a deformation of 0.5% $\gamma$ from –80° C. to –10° C. and 2% $\gamma$ from –10° C. to 100° C.

Mooney Viscosity: Mooney viscosity measurements were conducted according to ASTM-D 1646-89.

EXAMPLES

Representative Alkylaminosilane Compound

Example 1

Bis-(dimethylamino)phenylmethylsilane was treated with sec-butyllithium (s-BuLi) to effect lithiation, in the manner below, providing a compound having structure A:

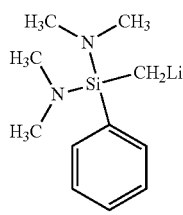

The following ingredients were charged to a 300 mL, dry, nitrogen-purged bottle fitted with a crown seal and nitrile cap liner: bis-(dimethylamino) phenylmethylsilane, 9.23 mmol (2.0 mL, 1.92 g); triethylamine, 5.0 mL; sec-butyllithium, 10.1 mmol (7.2 mL of 1.4M solution in cyclohexane). The resulting solution was agitated for 2.5 hrs at 50° C., and was estimated to be approximately 0.65M in compound A.

Example 2

The freshly metallated reagent of Example 1 was used to polymerize 1,3-butadiene in a sealed bottle. A polymer of $M_n$=25 kg/mol was targeted. An 800 mL bottle (dried, purged, and fitted as in Example 1) was charged with 31.4 g of 1,3-butadiene in 261 g of anhydrous hexanes, and 2.0 mL (ca. 1.3 mmol) of the reagent of Example 1 was then injected into the bottle. The bottle was agitated at 50° C. for 75 min, then allowed to cool to room temperature overnight. The resulting cement was quenched with 2 mL of 2-propanol (i-PrOH), and stabilized with di-t-butyl-p-cresol (DBPC). From the solids content, a conversion of 90% was estimated. The cement was coagulated in ethanol, and the coagulate was re-dissolved in hexanes, then re-coagulated twice more in the same manner. The coagulated polymer was dried at room temperature under a stream of nitrogen for four hrs, then under vacuum at ca. 70° C. overnight. The polybutadiene (PBD) product had $M_n$=26.9 kg/mol as determined by SEC. NMR ($^{13}$C) analysis of the product showed nearly quantitative incorporation of the silyl group (the ratio of carbons in the Si—CH$_2$ region (11.612.04 ppm) to those from terminal CH$_3$ (trans, 18.1 ppm; cis, 13.0 ppm) was nearly 1:1).

Examples 3-5

Another freshly metallated reagent was prepared as in Example 1 and used to polymerize 1,3-butadiene and mixtures of styrene and 1,3-butadiene in sealed bottles. The polymerization procedure and workup of Example 2 was followed, except that the time of the polymerizations was 120 min. These polymerizations targeted a 125 kg/mol PBD (Example 3: found $M_n$=139.2 kg/mol), and 25 and 125 kg/mol styrene-butadiene copolymers (SBRs) (found $M_n$=35.6 and 211.1 kg/mol, Examples 4 and 5, respectively). The polymerizations of Examples 3, 4 and 5 proceeded in conversions of 80%, 97% and 96%, respectively.

Example 6 (Pre-Mixed, Batch)

A solution in hexanes of the freshly lithiated reagent of bis-(dimethylamino)phenylmethylsilane of approximate concentration 0.65M was prepared as in Example 1. It was used to initiate copolymerization of styrene with 1,3-butadiene with target $M_n$=120 kg/mol, in a batch reactor under anhydrous nitrogen atmosphere, according to the following procedure. A stirred, 7.6-L autoclave-type reactor was charged with 3755 g of anhydrous hexanes, 551.1 g of anhydrous 1,3-butadiene, 129.3 g of anhydrous styrene, and 1.2 mL of a 1.60M solution of oligomeric oxolanyl propanes in hexanes. The mixture was held at a steady temperature of 49° C., and 8.72 mL (5.67 mmol) of the lithiated bis-(dimethylamino)phenylmethylsilane solution was added. After reaching a peak temperature of 55.2° C., the polymerization was allowed to continue for an additional 60 min, reaching 92% conversion, as estimated from the solids content of the cement. Samples of the product cement were collected through a needle into dried, purged, sealed 800 mL bottles. Each was quenched with 2 mL of nitrogen-sparged 2-propanol and stabilized with DBPC, and thereafter coagulated in 2-propanol containing added DBPC. The combined coagulates were drum-dried on a two-roll mill at 110° C., yielding Sample No. 6. Properties are summarized in TABLE 1, below.

Example 7 (Pre-Mixed, Semi-Batch)

Copolymerization of styrene with 1,3-butadiene was carried out under metered, semi-batch conditions in a stirred batch reactor with anhydrous nitrogen atmosphere, according to the following procedure, with target $M_n$=140 kg/mol. A stirred, 7.6 L autoclave-type reactor was charged with 1710 g of anhydrous hexanes and 0.27 mL of a 1.60M solution of oligomeric oxolanyl propanes in hexanes. The mixture was heated to and held at 85° C. Then a mixture of 217.7 g of anhydrous styrene and 462.7 g of anhydrous 1,3-butadiene in 2063.4 g of anhydrous hexanes was added to the reactor at approximately 36 g/min, by use of a meter. After about ten minutes of metering, 7.48 mL (4.86 mmol) of the 0.65M lithiated bis-(dimethylamino)phenylmethylsilane solution (prepared freshly according to Example 1) was added. Metered addition of monomers was continued for 62 min after charging initiator. Then, samples of the product cement were collected through a needle into ten dried, purged, sealed 800 mL bottles. A conversion in the polymerization of 87.4% was estimated from the solids content of the cement. The cements in five of the bottles were quenched, stabilized, coagulated and dried as in Example 6, yielding Sample 7. Properties are summarized in TABLE 1, below.

Example 8 (Pre-Mixed, Semi-Batch)

The cements in the remaining five bottles of Example 7 were each treated with a solution of 0.2M SnCl$_4$ at 0.6 equiv. of Sn—Cl per Li, and then agitated at 50° C. for 35 min. After agitation, the cements were quenched, stabilized, coagulated and dried as in the above Examples, to yield Sample 8. Properties are summarized in TABLE 1, below.

Example 9 (Pre-Mixed, Batch)

The procedure of Example 6 was repeated. The polymerization proceeded at 93.4% conversion. The product was worked up as in Example 6, to yield Sample 9, whose properties are included in TABLE 1, below.

Comparative Example A (Batch Control)

The procedure of Example 6 was followed, with the exception that n-butyl lithium was the only initiator. The polymerization proceeded at 96.6% conversion. The product was worked up as in Example 6, to yield Sample 10, whose properties are included in TABLE 1, below. Sample A was used a control batch polymer for comparative examples.

Comparative Example A' (Batch Control)

The procedure of Comparative Example A was followed, yielding a polymer with very similar properties, designated as Sample A', whose properties are included in TABLE 1, below. Sample A' also was used as a control batch polymer for comparative examples.

Comparative Example B (Semi-Batch Control)

The metered, semi-batch polymerization procedure of Example 7 was followed, with the exception that n-butyl lithium was the only initiator. The extent of conversion was not measured. The product was worked up as in Example 6, to yield Sample B, whose characterization is included in TABLE 1, below. Sample B was used as a control semi-batch polymer for comparative examples.

using an "all silica" formulation. Component parts by weight, per 100 parts of rubber (phr) are set forth in TABLE 2, below.

TABLE 2

| Ingredient | Amount (phr) |
|---|---|
| Master-batch Stage | |
| Test rubber | 80 |
| Natural rubber | 20 |
| Silica | 52.5 |
| Oil | 10.0 |
| Stearic acid | 2.0 |
| Wax | 2.0 |
| Antioxidant | 0.95 |
| Remill Stage | |
| Silica | 2.5 |
| Silane coupling agent | 5.0 |
| Final Stage | |
| Sulfur | 1.50 |
| Curatives | 4.1 |
| Zinc oxide | 2.50 |
| Total | 183.05 |

First, the polymer was placed in a 65-g Brabender mixer, and after 0.5 minutes, the remaining ingredients except the stearic acid were added. The stearic acid was then added after 3 minutes. The initial components were mixed for 5.5

TABLE 1

| Sample No. | SEC (THF) | | | $^1$H NMR | | | | |
|---|---|---|---|---|---|---|---|---|
| | $M_n$ (kg/mol) | PDI | % Cplg | % Sty | % Block Sty | %1,2 | %1,2 (BD = 100) | $T_g$ ° C. (DSC, Mdpt) |
| 6 | 131 | 1.05 | nil | 21.6 | 1.2 | 41.3 | 52.7 | −35.4 |
| 7 | 168.6 | 1.25 | ca. 9 | 35.5 | 6.7 | 12.1 | 18.7 | −47.8 |
| 8 | 212.3 | 2.14 | 39.2 | " | " | " | " | " |
| 9 | 140.7 | 1.06 | 1.6 | 20.9 | 1 | 43.9 | 55.6 | −33 |
| A | 117.1 | 1.03 | 0.5 | 20.1 | 1.2 | 44 | 55 | −34.8 |
| A' | 114.2 | 1.04 | nil | na | na | na | na | −35.1 |
| B | 176.7 | 1.17 | <9 | 35.3 | 4.3 | 12.5 | 19.2 | −43.9 |

Although the examples shown above used initiator A, reagents with similar effectiveness can be generated in a similar fashion from other substrates. For example, a lithiated species generated by treatment of bis-(hexamethyleneimino)octylmethylsilane with sec-butyllithium was used to initiate polymerization of 1,3-butadiene and copolymerization of 1,3-butadiene and styrene (as in Examples 2 and 4 above), producing polymers in 86% and 97.6% conversion, respectively. Targeting a molecular weight of 25 kg/mol in each case, the products obtained had $M_n$ by SEC of 30.5 and 33.2 kg/mol, respectively. Therefore, a range of other structures are effective as well.

In summary, the anionic copolymerizations of 1,3-butadiene and styrene employing A as initiator proceeded at high conversion to produce high molecular weight elastomers. The products were obtained at molecular weights at or near those targeted. The polymers incorporate silicon at the head group, with Si bonded to the polymer chain through a carbon atom.

The polymers were subsequently compounded with other ingredients to prepare vulcanizable elastomeric compounds, minutes. At the end of mixing the temperature was approximately 165° C. Each sample was transferred to a mill operating at a temperature of 60° C., where it was sheeted and subsequently cooled to room temperature. The mixtures were re-milled for 3.5 minutes at 130° C., whereby coupling agents were added under milder conditions than those of the masterbatch stage. Each sample was again transferred to a 60° C. mill, sheeted, and cooled to room temperature. The final components were mixed by adding the remilled mass and the curative materials to the mixer simultaneously. The initial mixer temperature was 65° C., while operating at 45 rpm. The final material was removed from the mixer after 2.5 minutes when the material temperature was between 100° C. and 105° C. The finals were sheeted into Dynastat buttons and 15×15×0.1875 cm sheets. The samples were cured at 171° C. for 15 minutes in standard molds placed in a hot press.

The results of compounded evaluations of the test samples and comparative samples are summarized in TABLE 3, below.

TABLE 3

| Ex. No. | Polymer Sample No. | ML1 + 4 (130° C.) | Dynastat tanδ, 60° C. | Strain Sweep (60° C., 5% γ, 10 Hz) tanδ | Strain Sweep (60° C., 5% γ, 10 Hz) ΔG' (MPa) | Temp. Sweep (60° C., 2% γ, 10 Hz) tanδ |
|---|---|---|---|---|---|---|
| 10 | A' | 14.2 | 0.1246 | 0.1446 | 4.7647 | 0.1347 |
| 11 | 6 | 20 | 0.1120 | 0.1368 | 4.8560 | 0.1222 |
| 12 | A' | 18.9 | 0.1166 | 0.1564 | 4.3799 | 0.1381 |
| 13 | 6 | 24.3 | 0.1118 | 0.1380 | 4.3526 | 0.1135 |
| 14 | A' | 15.4 | 0.1272 | 0.1558 | 4.4209 | 0.1348 |
| 15 | 9 | 23.9 | 0.1076 | 0.1382 | 4.0547 | 0.1031 |
| 16 | B | 49.8 | 0.1077 | 0.1400 | 5.5029 | 0.1267 |
| 17 | 7 | 74.6 | 0.1040 | 0.1375 | 4.8070 | 0.1207 |
| 18 | 8 | 92.1 | 0.1137 | 0.1378 | 4.0719 | 0.1175 |

The data in TABLE 3 show appreciable reductions in hysteresis at 60° C. for compounds prepared with elastomers using initiator A, when judged against the comparative examples which used n-butyl lithium initiator. The hysteresis reductions were greater among the polymers made under batch polymerization conditions (Samples 6 and 9), rather than under semi-batch conditions (Samples 7 and 8).

Comparative Sample C (Control Semi-Batch)

Copolymerization of styrene with 1,3-butadiene was carried out under metered, semi-batch conditions in a stirred batch reactor with anhydrous nitrogen atmosphere, according to the following procedure, with target $M_n$=140 kg/mol. A stirred, 7.6 L autoclave-type reactor was charged with 1710 g of anhydrous hexanes and 0.27 mL of a 1.60M solution of oligomeric oxolanyl propanes in hexanes. The mixture was heated to and held at 93.3° C. Then a mixture of 217.7 g of anhydrous styrene and 462.7 g of anhydrous 1,3-butadiene in 2063.4 g of anhydrous hexanes was added to the reactor at approximately 36 g/min, by use of a meter. After about ten minutes of metering, 2.86 mL (4.86 mmol) of 1.6M n-BuLi diluted with 25 mL of anhydrous hexanes was charged to the reactor. Metered addition of monomers was continued for 62 min after charging initiator, then samples of the product cement were collected through a needle into dried, purged, 800 mL sealed bottles. The cements in the bottles were each quenched, stabilized, coagulated and dried as for Sample A, yielding Sample C. Properties are summarized in TABLE 4, below.

Tris-(dimethylamino)methylsilane (structure B above) was treated with sec-butyllithium (s-BuLi) to effect lithiation. The following ingredients were charged to a 300 mL, dry, nitrogen-purged bottle fitted with a crown seal and nitrile cap liner: tris-(dimethylamino)methylsilane, 9.7 mmol (2.0 mL, 1.92 g); triethylamine, 4.0 mL; sec-butyllithium, 10.1 mmol (7.8 mL of 1.3M solution in cyclohexane). The resulting solution was agitated for 2 hrs at 50° C., and was estimated to be approximately 0.73M in lithiated reagent.

Example 19B (Pre-Mixed, Batch)

The procedure for Sample A was utilized to generate styrene-butadiene copolymer. However, this time lithiated tris-(dimethylamino)methylsilane (structure B) was used as the initiator, by preparing the lithiated reagent as in Example 19A and thereafter immediately charging it to the reactor. The temperature peaked at 56.7° C. and polymerization proceeded for another 60 minutes thereafter, and reached 88% conversion. The cement was collected in 800 mL bottles, which were each quenched with 2 mL of nitrogen-sparged ethanol and stabilized with DBPC, and thereafter coagulated in 2-propanol containing added DBPC. The combined coagulates were drum-dried on a two-roll mill at 110° C., yielding Sample 19, whose properties are included in TABLE 5, below.

TABLE 4

| Sample No. | SEC (THF) Mn (kg/mol) | SEC (THF) PDI | SEC (THF) % HMW | ¹H NMR % Sty | ¹H NMR % Block Sty | ¹H NMR %1,2 | ¹H NMR %1,2 (BD = 100) | Tg° C. (DSC, Mdpt) |
|---|---|---|---|---|---|---|---|---|
| A | 117.1 | 1.03 | 0.5 | 20.1 | 1.2 | 44 | 55 | −34.8 |
| C | 165.4 | 1.2 | 7.2 | 34.7 | 5 | 11.8 | 18.1 | −46.6 |

Additional Examples Using Metallated Aminosilane Initiators

Example 19A (Lithiated Initiator Workup)

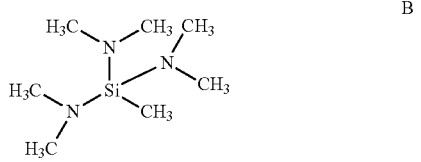

B

Example 20 (Pre-Mixed, Batch)

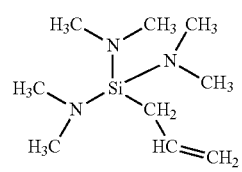

C

The procedure for Sample A was utilized to generate styrene-butadiene copolymer. However, this time 1.21 mL of neat tris-(dimethylamino)allylsilane (structure C above) was mixed with 3.34 mL of 1.6M n-BuLi and diluted to 50 mL with anhydrous hexanes, and the resulting mixture was charged immediately to the reactor. The temperature peaked at 58.9° C. and polymerization proceeded for another 60 minutes thereafter, and reached greater than 90% conversion. The cement was collected in 800 mL bottles, which were each quenched with 2 mL of nitrogen-sparged ethanol and stabilized with DBPC, and thereafter coagulated in 2-propanol containing added DBPC. The combined coagulates were drum-dried on a two-roll mill at 110° C., yielding Sample 20, whose properties are included in TABLE 5, below.

Example 21 (Pre-Mixed, Semi-Batch)

The procedure for Sample C was utilized to generate styrene-butadiene copolymer. However, the initiator used in this case consisted of a mixture of 2.0 mL mL of 9.7M tris-(dimethylamino)methylsilane (structure B above), 4 mL of neat triethylamine, and 7.8 mL of 1.3M sec-butyllithium in cyclohexane, which was agitated for 2.5 hrs at 50° C. (~0.73M in lithiated reagent), and thereafter charged to the reactor. Polymerization temperature was maintained between about 85° C. to about 95° C., and the metering was stopped about 120 minutes later. As above, the product cement was collected into 800 mL bottles, and each was quenched, stabilized, coagulated and dried as for Sample C, yielding Sample 21. Properties are summarized in TABLE 5, below.

Example 22 (Pre-Mixed, Semi-Batch)

The procedure for Sample C was utilized to generate styrene-butadiene copolymer. However, the initiator used in this case consisted of a mixture of 0.96 mL of 4.44M tris-(dimethylamino)allylsilane (structure C above) in hexanes and 2.65 mL of 1.6M n-BuLi, which was diluted to 25 mL with anhydrous hexanes. The initiator was charged to the reactor immediately after mixing. Polymerization temperature was maintained between about 85° C. to about 95° C., and the metering was stopped about 120 minutes later. As above, the product cement was collected into 800 mL bottles, and each was quenched, stabilized, coagulated and dried as for Sample C, yielding Sample 22. Properties are summarized in TABLE 5, below.

TABLE 5

| Sample No. | Mn (kg/mol) | PDI | % Cplg | Tg° C. (DSC, Mdpt) |
| --- | --- | --- | --- | --- |
| 19 | 114 | 1.05 | 0.5 | −38.6 |
| 20 | 111 | 1.03 | — | −35.4 |
| 21 | 166 | 1.53 | 94.2 | −48.6 |
| 22 | 175 | 1.52 | 6 | −50.3 |

The copolymers were thereafter compounded with to prepare vulcanizable elastomeric compounds, as disclosed in TABLE 2, above. Testing of the compounded rubber yielded the results listed in TABLE 6, below.

TABLE 6

| Ex. No. | Sample No. | ML1 + 4 (130° C.) | Tensile (Mpa) | Elong. (%) | Strain Sweep (60° C., 5% γ, 10 Hz) | | Temp. Sweep (60° C., 2% γ, 10 Hz) | |
| --- | --- | --- | --- | --- | --- | --- | --- | --- |
| | | | | | tanδ | ΔG' (MPa) | tanδ | Tg (° C.) |
| 23 | A | 17.6 | 12.8 | 333 | 0.1553 | 4.31 | 0.1362 | −21.8 |
| 24 | 19 | 20.0 | 15.1 | 380 | 0.1392 | 4.37 | 0.1317 | −23.4 |
| 25 | 20 | 16.5 | 14.5 | 315 | 0.1496 | 4.29 | 0.1279 | −20.8 |
| 26 | C | 55.8 | 16.1 | 380 | 0.1476 | 4.38 | 0.1270 | −27.4 |
| 27 | C | 51.8 | 18.9 | 367 | 0.1371 | 5.10 | 0.1293 | −28.1 |
| 28 | 21 | 84.8 | 13.9 | 260 | 0.0828 | 1.52 | 0.0727 | −23.9 |
| 29 | 22 | 84.4 | 21.1 | 398 | 0.1367 | 4.49 | 0.1284 | −28.0 |

The data in TABLE 6 show consistent improvements in hysteresis properties for polymers that incorporate a metallated aminosilane initiator per the methods described herein.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

We claim:

1. An aminosilane functionalized polymer comprising at least one aminosilane group at its head only, where the at least one aminosilane group at the head comprises residue from the reaction product of
   (a) at least one metallating agent, and
   (b) at least one alkylaminosilane compound selected from either bis-(dialkylamino)phenylmethylsilane, bis-(hexamethyleneimino)phenylmethylsilane, tris-(dialkylamino)allylsilane, tris-(dialkylamino)alkylsilane wherein the alkyl on the silane is selected from methyl, ethyl, or propyl and combinations thereof
   or from

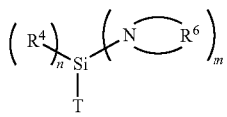

(IB)

where n is a whole number selected from the group consisting of 0 and 1, and m is a whole number selected from the group consisting of 2-3, with the proviso that the sum of m and n equals 3; where T is a methyl, ethyl, propyl, or allylic group; where each $R^4$ is independently a hydrocarbyl group; where each $R^6$ is independently a hydrocarbylene and where the aminosilane functionalized polymer is polymerized from at least one anionically polymerizable monomer comprising 1,3-butadiene with a metalating agent to monomer molar ratio of 1:10 to 1:20,000;

where the aminosilane functionalized polymer does not have two or more living polymer chains coupled together with a coupling agent selected from formula (1) $R*_nM^1Y_{(4-n)}$ where each $R*$ is independently a monovalent organic group having 1 to 20 carbon atoms, $M^1$ is a tin, silicon or germanium atom, Y is a halogen atom and n of formula (1) is an integer of 0-3; and where the aminosilane functionalized polymer has a Mn of greater than 25 kg/mole to about 200 kg/mole.

2. The polymer of claim 1, where the at least one metallating agent is selected from the group consisting of hydrocarbyl lithium compounds, hydrocarbyl sodium compounds, hydrocarbyl potassium compounds, hydrocarbyl magnesium compounds, and combinations thereof.

3. The polymer of claim 1, where the at least one metallating agent comprises a first component and a second component, where the first component is a Lewis base and the second component is selected from the group consisting of hydrocarbyl lithium compounds, hydrocarbyl sodium compounds, hydrocarbyl potassium compounds, hydrocarbyl magnesium compounds, and combinations thereof.

4. The polymer of claim 1, where the at least one metallating agent comprises a first component and a second component, where the first component is selected from the group consisting of alkali metal alkoxide, alkali metal arylsulfonate, and combinations thereof, and where the second component is selected from the group consisting of hydrocarbyl lithium compounds, hydrocarbyl sodium compounds, hydrocarbyl potassium compounds, hydrocarbyl magnesium compounds, and combinations thereof.

5. The polymer of claim 1, where the at least one alkylaminosilane compound consists of bis-(dialkylamino)phenylmethylsilane.

6. The polymer according to claim 1, wherein the at least one anionically polymerizable monomer further comprises styrene and the polymer is styrene-butadiene copolymer.

7. The polymer according to claim 5, wherein the at least one anionically polymerizable monomer further comprises styrene and the polymer is styrene-butadiene copolymer.

8. The polymer according to claim 1, wherein the polymer is polybutadiene.

9. The polymer according to claim 5, wherein the polymer is polybutadiene.

10. The polymer according to claim 1, wherein the polymer comprises a proton from a quenching agent at its tail.

11. The polymer according to claim 10, wherein the quenching agent comprises an alcohol, water, or a combination thereof.

12. An aminosilane functionalized polymer comprising at least one aminosilane group at its head only, where the at least one aminosilane group at the head comprises residue from the reaction product of
    (a) at least one metallating agent, and
    (b) at least one alkylaminosilane compound selected from bis-(dialkylamino)phenylmethylsilane, bis-(hexamethyleneimino)phenylmethylsilane, tris-(dialkylamino)allylsilane, tris-(dialkylamino)alkylsilane wherein the alkyl on the silane is selected from methyl, ethyl, or propyl and combinations thereof, and
where the aminosilane functionalized polymer is polymerized from at least one anionically polymerizable monomer comprising 1,3-butadiene with a metalating agent to monomer molar ratio of 1:10 to 1:20,000;

where the aminosilane functionalized polymer does not have two or more living polymer chains coupled together with a coupling agent selected from formula (1) $R*_nM^1Y_{(4-n)}$ where each $R*$ is independently a monovalent organic group having 1 to 20 carbon atoms, $M^1$ is a tin, silicon or germanium atom, Y is a halogen atom and n of formula (1) is an integer of 0-3; and where the aminosilane functionalized polymer has a Mn of greater than 25 kg/mole to about 200 kg/mole.

13. The polymer according to claim 12, wherein the at least one anionically polymerizable monomer further comprises styrene and the polymer is styrene-butadiene copolymer.

14. The polymer according to claim 12, wherein the polymer is polybutadiene.

15. The polymer according to claim 12, wherein the polymer comprises a proton from a quenching agent at its tail and the quenching agent comprises an alcohol, water, or a combination thereof.

16. The polymer of claim 12, where the at least one metallating agent is selected from the group consisting of hydrocarbyl lithium compounds, hydrocarbyl sodium compounds, hydrocarbyl potassium compounds, hydrocarbyl magnesium compounds, and combinations thereof.

17. An aminosilane functionalized polymer comprising at least one aminosilane group at its head only, where the at least one aminosilane group at the head comprises residue from the reaction product of
    (a) at least one metallating agent, and
    (b) at least one alkylaminosilane compound having the formula

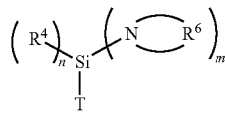
(IB)

where n is a whole number selected from the group consisting of 0 and 1, and m is a whole number selected from the group consisting of 2-3, with the proviso that the sum of m and n equals 3; where T is a methyl, ethyl, propyl, or allylic group; where each $R^4$ is independently a hydrocarbyl group; where each $R^6$ is independently a hydrocarbylene, and where the aminosilane functionalized polymer is polymerized from at least one anionically polymerizable monomer comprising 1,3-butadiene with a metalating agent to monomer molar ratio of 1:10 to 1:20,000;

where the aminosilane functionalized polymer does not have two or more living polymer chains coupled together with a coupling agent selected from formula (1) $R^*_n M^1 Y_{(4-n)}$ where each R* is independently a monovalent organic group having 1 to 20 carbon atoms, $M^1$ is a tin, silicon or germanium atom, Y is a halogen atom and n of formula (1) is an integer of 0-3; and where the aminosilane functionalized polymer has a Mn of greater than 25 kg/mole to about 200 kg/mole.

18. The polymer according to claim 17, wherein the at least one anionically polymerizable monomer further comprises styrene and the polymer is styrene-butadiene copolymer.

19. The polymer according to claim 17, wherein the polymer is polybutadiene.

20. The polymer according to claim 17, wherein the polymer comprises a proton from a quenching agent at its tail and the quenching agent comprises an alcohol, water, or a combination thereof.

21. The polymer of claim 17, where the at least one metallating agent is selected from the group consisting of hydrocarbyl lithium compounds, hydrocarbyl sodium compounds, hydrocarbyl potassium compounds, hydrocarbyl magnesium compounds, and combinations thereof.

* * * * *